United States Patent [19]

Hötzel

[11] 4,439,449

[45] Mar. 27, 1984

[54] MEDICAMENT FOR DIMINUTION OF OXALATE DEVELOPMENT AND EXCRETION IN URINE

[75] Inventor: Dieter Hötzel, Sankt Augustin, Fed. Rep. of Germany

[73] Assignee: Dr. Madaus & Co., Cologne, Fed. Rep. of Germany

[21] Appl. No.: 324,502

[22] Filed: Nov. 24, 1981

Related U.S. Application Data

[63] Continuation of Ser. No. 957,968, Nov. 6, 1978, abandoned.

[30] Foreign Application Priority Data

Nov. 5, 1977 [DE] Fed. Rep. of Germany ....... 2749618

[51] Int. Cl.³ ............................................. A61K 31/19
[52] U.S. Cl. .................................... 424/317; 424/251; 424/255; 424/263
[58] Field of Search ................ 424/317, 255, 263, 251

[56] References Cited

U.S. PATENT DOCUMENTS 3,164,524  1/1965  Fand et al. .......................... 424/317

OTHER PUBLICATIONS

Husa's–*Pharmaceutical Dispensing*, Sixth Edition, Mack Pub. Co., Easton, Pa., 1966; pp. 732 and 742.

*Primary Examiner*—Frederick E. Waddell
*Attorney, Agent, or Firm*—Felfe & Lynch

[57] ABSTRACT

A method for the treatment of undesired uroliths with benzoic acid is disclosed.

8 Claims, No Drawings

MEDICAMENT FOR DIMINUTION OF OXALATE DEVELOPMENT AND EXCRETION IN URINE

This is a continuation, of application Ser. No. 957,968, filed Nov. 6, 1978, now abandoned.

The formation of uroliths in the kidney and in the vesicle can up to now not be diminished or even avoided successfully. There are different kinds of uroliths. An essential part thereof are oxalate calculus.

The formation of oxalate calculus is due to various factors. The oxalate being present in the human body is partially taken up with the food. This is called the exogenous or alimentary oxalate respectively. The external supply of oxalate can be controlled and regulated in a rather simple manner.

A second portion of oxalate in the human body is the so called endogenous oxalate which develops as a side product from the intermediary metabolism. The oxalate has no important function within the metabolism, thus it can be considered as a side product. However, this side product is highly unwelcome, among others it may lead to the formation of uroliths.

The object of the present invention is to diminish or even to eliminate the formation of uroliths.

To accomplish this object, the invention operates on the assumption that oxalate formation can be controlled by controlling the substrates necessary for its formation. More specifically, by binding the required substrates and otherwise biochemically reacting them, they are no longer available in a substantial extent for an oxalate formation.

An essential substrate for oxalate formation is glycine. It is converted in the human body into oxalate during different steps which include also the formation of glycol aldehyde, glycolic acid, and glyoxylic acid.

The invention has realized that the above mentioned problem can be solved by means of a pharmaceutic preparation containing benzoic acid, derivatives or salts thereof. These substances, preferably benzoic acid, are appropriate to react with glycine, and to form proportionately benzoyl-glycine, also called hippuric acid, which can easily be eliminated with the urine. With a suitable dosage one can draw away enough glycine so that only a minimum of glyoxylate develops. The direct result of this is to reduce also the possibility of formation of oxalate calculus.

The use of benzoic acid as an urologic remedy requires first the consideration of possible toxicity. However, this is believe to be no problem as benzoic acid is presently widely used as a preservative in foodstuffs, and toxicity determinations made with respect to foodstuff indicate that amounts required for the invention are well below toxicity levels.

The use of the proposed medicament is mainly effective in relapse-prophylaxis with urolithiasis, not, however, for example for a therapy or prophylaxis of the innate hyperoxaluria. The use according to the invention refers especially to relapse-prophylaxis for people being liable to oxalate calculus.

With respect to various derivatives of the benzoic acid which have been mentioned in connection with the proposed medicament, it is noted that the molecular structure of the pure benzoic acid may be altered in as far as other molecular groups are added for example in the ortho-, meta-, or para-position, which do not affect the reaction with glycine and the development of benzoyl glycine.

It was mentioned already that the formation of glyoxylate is an intermediate stage in the development of oxalate.

It is also possible to still reduce the development of oxalate, at least at certain parts, in that the glyoxylate is absorbed or used up in another way. This occurs self-acting at a small part within the scope of the metabolism in form of a biosynthesis by which then emerges formyl co-emzyme A. This conversion is caused by folate. Thus when folate is added to the inventive medicament the portion of the glyoxylate which has been absorbed in that way can be increased, and thus the formation of oxalate is reduced.

It is furthermore advantageous to add to the medicament vitamins of the pyridoxine-group, whereby an amination of glyoxylate to glycine is reached, and glycine may then be absorbed by benzoic acid and/or its derivatives.

Adding thiamine can also be of advantage since herewith a biosynthesis of glyoxylate to alpha-keto-beta-OH-adipic acid is activated. That means that also herewith a further portion of glyoxylate is hindered in forming oxalate.

Addition of pantothenic acid is advisable in order to stimulate the biosynthesis of benzoyl glycine when adding benzoic acid and/or its derivatives.

The aim of the proposed combination of agents is in principle to influence the metabolism balance during the decisive biochemical reactions in such a way that the metabolism is diverted from the biosynthesis of the oxalate.

It can furthermore be advantageous to eliminate a local factor of urolith formation with retinole which may therefore also be contained in the proposed medicament.

It is, of course, conceivable to still add other known urologic media as active agents to the proposed medicament.

The dosage for obtaining the required effect with adult persons is generally within a scope of between 400 and 1000 mg of benzoic acid or the equivalent quantities of derivatives of salts for a period of 24 hours.

For this period the pharmaceutical preparation may contain as additional active agents for example the following quantities of vitamins:

0.9–1.8 mg retinole (vitamin A)
1–3 mg thiamine (vitamin $B_1$)
1–3 mg pyridoxine (vitamine $B_6$)
0.4–1 mg folate
5–10 mg pentothenic acid The dosage will have to be adjusted, of course, to the physiologic condition and medical evidence of the corresponding person.

What we claim is:

1. Method for the relapse-prophylactive treatment of undesired uroliths, which method comprises treating a subject with an effective amount of benzoic acid.

2. Method as claimed in claim 1 wherein said benzoic acid is administered in conjunction with a vitamin selected from the group consisting of pyridoxine vitamins, thiamine, folate, pantothenic acid and retinole.

3. Method as claimed in claim 2 wherein said vitamin is folate.

4. Method as claimed in claim 2 wherein said vitamin is pyridoxine (vitamin $B_6$).

5. Method as claimed in claim 2 wherein said vitamin is thiamine.

6. Method as claimed in claim 2 wherein said vitamin is retinole (vitamin A).

7. Method as claimed in claim 2 wherein said vitamin is pantothenic acid.

8. Method for the relapse-prophylactive treatment of undesired uroliths, which method comprises treating a subject with a pharmaceutical composition comprising:

400 to 1,000 mg of benzoic acid
0.9–1 mg retinole (vitamin A)
1–3 mg thiamine (vitamin B1)
1–3 mg pyridoxine (vitamin B6)
0.1–1 mg folate
5–10 mg pantothenic acid.

* * * * *